(12) United States Patent
Iwaisako

(10) Patent No.: US 10,321,811 B2
(45) Date of Patent: Jun. 18, 2019

(54) OPTICAL TRANSMISSION MODULE, IMAGING APPARATUS, AND OPTICAL TRANSMISSION MODULE STRUCTURE

(71) Applicant: OLYMPUS CORPORATION, Tokyo (JP)

(72) Inventor: Hiroshi Iwaisako, Shiojiri (JP)

(73) Assignee: OLYMPUS CORPORATION, Tokyo (JP)

( * ) Notice: Subject to any disclaimer, the term of this patent is extended or adjusted under 35 U.S.C. 154(b) by 0 days.

(21) Appl. No.: 15/710,128

(22) Filed: Sep. 20, 2017

(65) Prior Publication Data

US 2018/0008123 A1 Jan. 11, 2018

Related U.S. Application Data

(63) Continuation of application No. PCT/JP2015/059646, filed on Mar. 27, 2015.

(51) Int. Cl.
*A61B 1/00* (2006.01)
*A61B 1/04* (2006.01)
(Continued)

(52) U.S. Cl.
CPC .......... *A61B 1/0017* (2013.01); *A61B 1/0011* (2013.01); *A61B 1/00117* (2013.01);
(Continued)

(58) Field of Classification Search
CPC combination set(s) only.
See application file for complete search history.

(56) References Cited

U.S. PATENT DOCUMENTS

| 4,725,128 A | 2/1988 | Bornzin et al. |
| 10,025,041 B2 * | 7/2018 | Tong .................... G02B 6/3861 |

(Continued)

FOREIGN PATENT DOCUMENTS

| JP | S59-048720 A | 3/1984 |
| JP | S61-105518 A | 5/1986 |

(Continued)

OTHER PUBLICATIONS

International Search Report dated Jun. 23, 2015 issued in PCT/JP2015/059646.

(Continued)

*Primary Examiner* — Omar R Rojas
(74) *Attorney, Agent, or Firm* — Scully, Scott, Murphy & Presser, P.C.

(57) ABSTRACT

An optical transmission module includes a substrate having an opening portion; an optical element closing an opening on the lower surface side of the substrate and converting an electric signal into an optical signal or the optical signal into the electric signal; an optical fiber transmitting the optical signal; a ferrule closing an opening on the upper surface side of the substrate and having an optical fiber insertion hole; and a resin filled into a space surrounded at least by the substrate, the optical element, the ferrule, and a distal end of the optical fiber, wherein the ferrule has a resin filling hole spaced apart from the optical fiber insertion hole to fill the space with the resin, and an angle formed by an axis of the optical fiber insertion hole and an axis of the resin filling hole is equal to or more than 0° and less than 90°.

16 Claims, 17 Drawing Sheets

(51) Int. Cl.
*G02B 6/42* (2006.01)
*A61B 1/05* (2006.01)
(52) U.S. Cl.
CPC .................. *A61B 1/04* (2013.01); *A61B 1/05* (2013.01); *G02B 6/4239* (2013.01); *G02B 6/4212* (2013.01); *G02B 6/4234* (2013.01); *G02B 6/4292* (2013.01)

(56) References Cited

U.S. PATENT DOCUMENTS

| | | |
|---|---|---|
| 2002/0118924 A1 | 8/2002 | Murata |
| 2004/0178462 A1 | 9/2004 | Sakaguchi et al. |

FOREIGN PATENT DOCUMENTS

| | | |
|---|---|---|
| JP | 2002-139633 A | 5/2002 |
| JP | 2002-250846 A | 9/2002 |
| JP | 2004-281530 A | 10/2004 |
| JP | 2012-198451 A | 10/2012 |
| JP | 2012-203326 A | 10/2012 |
| JP | 2013-007854 A | 1/2013 |
| JP | 2013-080069 A | 5/2013 |
| JP | 2014-010329 A | 1/2014 |

OTHER PUBLICATIONS

Japanese Office Action dated Mar. 5, 2019 in Japanese Patent Application No. 2017-508835.

\* cited by examiner

OPTICAL TRANSMISSION MODULE, IMAGING APPARATUS, AND OPTICAL TRANSMISSION MODULE STRUCTURE

This application is a continuing application of PCT International Application No. PCT/JP2015/059646 filed on Mar. 27, 2015, the content of which is incorporated herein by reference.

BACKGROUND OF THE INVENTION

Field of the Invention

The present invention relates to an optical transmission module, an imaging apparatus including the optical transmission module, and an optical transmission module structure.

Description of Related Art

Conventionally, in a medical endoscope, a lesion can be observed by deeply inserting an insertion unit into a body. As such an endoscope, there is an endoscope including an imaging apparatus in which an imaging element such as a CCD is built in a distal end of the insertion unit. In recent years, imaging elements with a large number of pixels enabling clearer image observation have been developed, and the use of such imaging elements with a large number of pixels in endoscopes has been studied. When an imaging element with a large number of pixels is used in an endoscope, in order to transmit a signal at high speed between the imaging element and the signal processing device, it is necessary to incorporate an optical transmission module into the endoscope.

Japanese Unexamined Patent Application Publication, First Publication No. 2012-198451 discloses an optical transmission module which includes a ferrule for holding an optical fiber, an optical element disposed on a front end side of the ferrule, an optical fiber insertion hole into which the optical fiber is inserted from a rear end side of the ferrule, and an adhesive containing portion continuously formed in the optical fiber insertion hole. In the process of manufacturing the optical transmission module, after the optical fiber insertion hole is filled with the adhesive (resin) using a filling needle, the optical fiber is inserted into the optical fiber insertion hole.

SUMMARY OF THE INVENTION

According to a first aspect of the present invention, an optical transmission module includes a substrate having an opening portion penetrating in a vertical direction orthogonal to a plane direction; an optical element which is disposed to close an opening on a lower surface side of the substrate and the optical element converts an electric signal into an optical signal or converts the optical signal into the electric signal; an optical fiber which transmits the optical signal; a ferrule which is disposed to close an opening on an upper surface side of the substrate and has an optical fiber insertion hole through which the optical fiber is inserted and held; and a resin filled into a space surrounded at least by the substrate, the optical element, the ferrule, and a distal end of the optical fiber. The ferrule has a resin filling hole formed to be spaced apart from the optical fiber insertion hole to fill the space with the resin, and an angle formed by an axis of the optical fiber insertion hole and an axis of the resin filling hole is equal to or more than 0° and less than 90°.

According to a second aspect of the invention, in the optical transmission module according to the first aspect, the ferrule may have a plurality of resin filling holes.

According to a third aspect of the invention, in the optical transmission module according to the first aspect, the ferrule may further include an air discharge hole which discharges the air in the space to the outside.

According to a fourth aspect of the invention, in the optical transmission module according to the second aspect, the ferrule may further include an air discharge hole which discharges the air in the space to the outside.

According to a fifth aspect of the invention, in the optical transmission module according to the third aspect, an end of the air discharge hole may be disposed in communication with the optical fiber insertion hole and close to the distal end of the optical fiber.

According to a sixth aspect of the invention, in the optical transmission module according to the first aspect, the substrate may have a through-hole extending in a direction orthogonal to the plane direction. The through-hole and the resin filling hole may communicate with each other.

According to a seventh aspect of the invention, in the optical transmission module according to the first aspect, an angle formed by the axis of the optical fiber insertion hole and the axis of the resin filling hole may be equal to or more than 22.5° and equal to or less than 67.5°.

According to an eighth aspect of the invention, in the optical transmission module according to the seventh aspect, the angle formed by the axis of the optical fiber insertion hole and the axis of the resin filling hole may be equal to or more than 45° and equal to or less than 60°.

According to a ninth aspect of the invention, in the optical transmission module according to the third aspect, the air discharge hole may communicate with the optical fiber insertion hole and may be formed along the optical fiber insertion hole.

According to a tenth aspect of the invention, an imaging apparatus includes an imaging element which picks up an image of a subject; and the optical transmission module according to any one of the first to ninth aspects which converts an imaging signal from the imaging element into an optical signal or converts the optical signal into an electric signal.

According to an eleventh aspect of the invention, an optical transmission module structure includes a substrate having an opening portion penetrating in a vertical direction orthogonal to a plane direction; an optical element which is disposed to close an opening on a lower surface side of the substrate and the optical element converts an electric signal into an optical signal or converts the optical signal into the electric signal; a ferrule which is disposed to close an opening on an upper surface side of the substrate and has an optical fiber insertion hole through which an optical fiber configured to transmit the optical signal is inserted and held; and a resin filled into a space surrounded at least by the substrate, the optical element, the ferrule, and a distal end of the optical fiber. The ferrule has a resin filling hole formed to be spaced apart from the optical fiber insertion hole to fill the resin in the space surrounded at least by the substrate, the optical element, the ferrule and the distal end of the optical fiber. An angle formed by an axis of the optical fiber insertion hole and an axis of the resin filling hole is equal to or more than 0° and less than 90°.

DETAILED DESCRIPTION OF THE INVENTION

Figure 1:
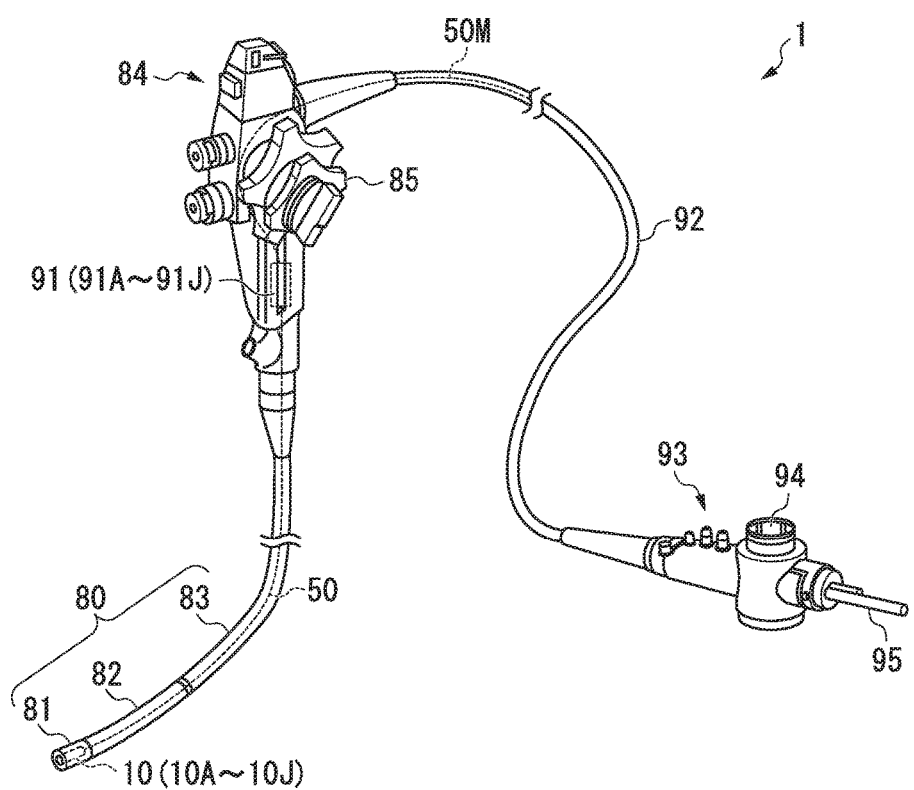
FIG. 1 is a schematic configuration view of an endoscope according to a first embodiment.

Hereinafter, as an embodiment of the present invention, a medical endoscope for picking up an image in a body cavity of a patient or the like will be described as an example. The present invention is not limited by this embodiment. In the drawings, the same parts are denoted by the same reference numerals. The drawings are schematic, and relationships between the thicknesses and widths of the members, the ratios of the members, and the like are different from actual ones. Also, in the drawings, portions having different dimensions and ratios are included.

First Embodiment

FIG. 1 is a schematic configuration view of an endoscope according to a first embodiment.

An endoscope 1 as an imaging apparatus includes an insertion unit 80, an operation unit 84 disposed on a proximal end portion side of the insertion unit 80, a universal cord 92 extending from the operation unit 84, and a connector 93 disposed on the proximal end side of the universal cord 92.

The insertion unit 80 includes a rigid distal end portion 81, a bent portion 82 for changing the direction of the rigid distal end portion 81, and an elongated flexible pliable portion 83.

In the operation unit 84, an angle knob 85 for operating the bent portion 82 is disposed, and an O/E converter 91 which is an optical transmission module for converting an optical signal into an electric signal is disposed.

The connector 93 has an electrical connector unit 94 connected to a processor (not shown) that performs image processing on the image acquired by the endoscope 1, and an light guide connection unit 95 connected to a light source (not shown). The light guide connection unit 95 is connected to an optical fiber bundle which guides the illumination light to the rigid distal end portion 81. In the connector 93, the electrical connector unit 94 and the light guide connection unit 95 may be integrated. Both of the electrical connector unit 94 and the light guide connection unit 95 that are integrated with each other, are connected to the processor. The processor and the light source are separately connected, and the illumination light emitted from the light source is supplied to the light guide connection unit 95 via the processor.

An imaging element 90, an E/O converter 10 that serves as an optical transmission module which converts an imaging signal output from the imaging element 90 from an electrical signal into an optical signal, and an optical fiber 50 are disposed in the rigid distal end portion 81. The imaging signal from the imaging element 90 is converted from an electric signal into an optical signal by the E/O converter 10, and is transmitted to the operation unit 84 via the optical fiber 50 inserted through the insertion unit 80. The optical signal is converted into an electric signal again by the O/E converter 91 disposed in the operation unit 84 and is transmitted to the electric connector unit 94 via the metal wiring 50M inserted through the universal cord 92. In the insertion unit 80 having a small diameter, an optical signal is transmitted via the optical fiber 50, and in the universal cord 92 which is not inserted into the body, an electric signal is transmitted via the metal wiring 50M.

When the O/E converter 91 is disposed in the electrical connector unit 94, the optical fiber 50 may be inserted through the universal cord 92 up to the electrical connector unit 94. When the O/E converter 91 is provided in the processor, the optical fiber 50 may be inserted to the connector 93.

Figure 2:
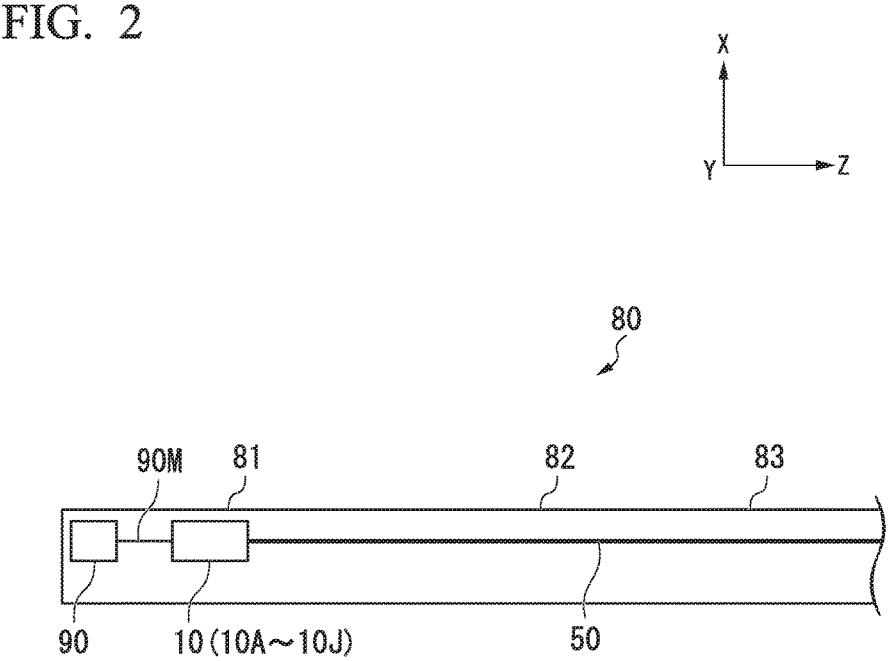
FIG. 2 is a schematic configuration view of an insertion section in the first embodiment.

FIG. 2 is a schematic configuration view of the insertion unit 80 in the first embodiment.

The imaging element 90, the E/O converter 10 for converting an imaging signal output from the imaging element 90 from an electric signal into an optical signal, and the optical fiber 50 are disposed in the rigid distal end portion 81. The imaging apparatus 90 is, for example, a complementary metal oxide semiconductor (CMOS) image sensor, a charge coupled device (CCD) image sensor, or the like.

The imaging signal from the imaging element 90 is transmitted to the E/O converter 10 by the metal wiring 90M. Further, the optical signal converted by the E/O converter 10 is transmitted to the O/E converter 91 by the optical fiber 50.

Next, the optical transmission module according to the first embodiment will be described with reference to FIGS. 3 and 4. Further, the E/O converter 10 will be described as an example of an optical transmission module.

Figure 3:
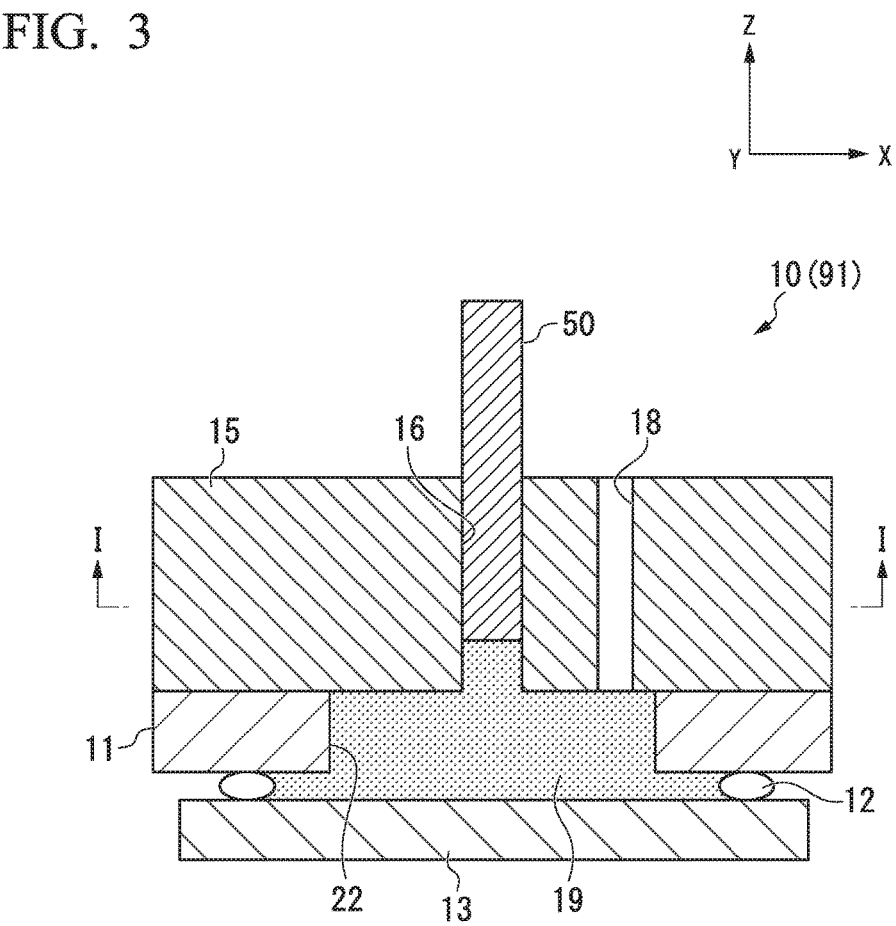
FIG. 3 is a cross-sectional view of an optical transmission module according to the first embodiment.
Figure 4:
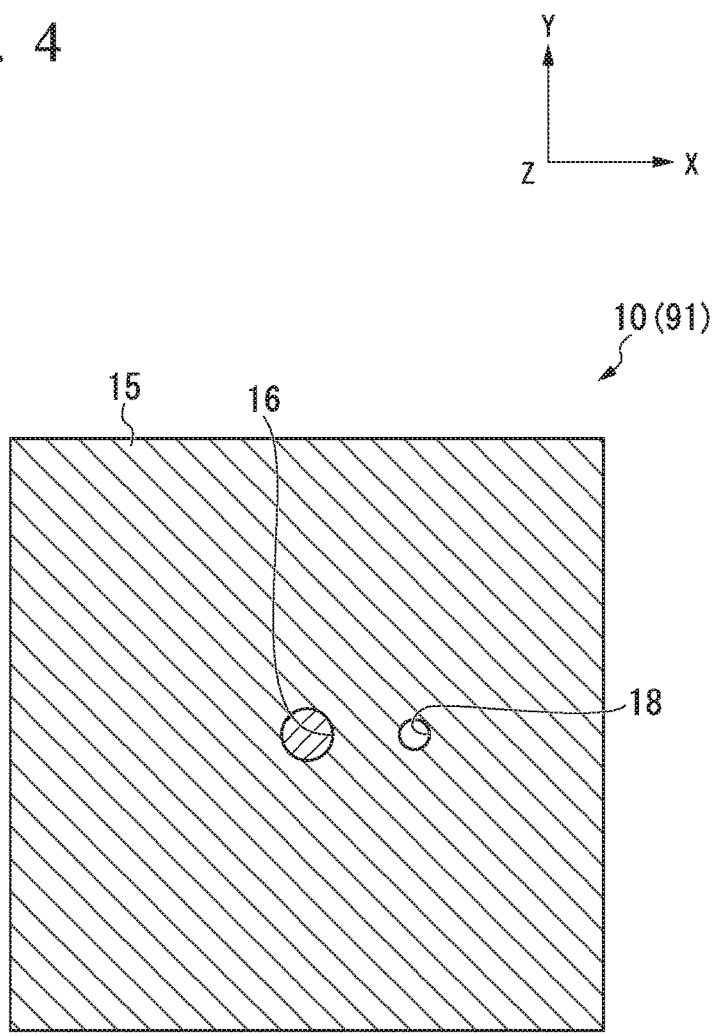
FIG. 4 is a cross-sectional view taken along a line I-I in FIG. 3.

FIG. 3 is a cross-sectional view of the optical transmission module according to the first embodiment. FIG. 4 is a cross-sectional view taken along a line I-I in FIG. 3.

The E/O converter 10 includes a substrate 11, a bump 12, an optical element 13, a ferrule 15, an optical fiber insertion hole 16, a resin filling hole 18, a resin 19, and an optical fiber 50.

The substrate 11 has an opening portion 22 in the vertical direction (Z direction) orthogonal to the plane direction. The optical element 13 is disposed on the substrate 11 to close the lower surface side opening of the substrate 11. The optical element 13 is electrically connected to the substrate 11 by the bump 12. The optical element 13 is, for example, a semiconductor laser element such as a vertical cavity surface emitting laser (VCSEL), and converts an imaging signal output from the imaging element 90 from an electric signal into an optical signal.

The ferrule 15 is disposed on the substrate 11 to close the upper surface side opening of the substrate 11. The ferrule 15 includes an optical fiber insertion hole 16 into which the optical fiber 50 is inserted, and a resin filling hole 18 for injecting the resin 19. The substrate 11 and the ferrule 15 may be directly connected to each other, or may be connected to each other via an adhesive layer or the like.

The optical fiber insertion hole 16 is a hole parallel to the Z direction. In the optical fiber insertion hole 16, the optical fiber 50 is inserted from the rear end side (the side on which the optical element 13 is not disposed) to the front end side (the side on which the optical element 13 is disposed). The shape of the I-I cross section of the optical fiber insertion hole 16 is circular.

The resin filling hole 18 is a hole parallel to the Z direction and is spaced apart from the optical fiber insertion hole 16. The shape of the I-I cross section of the resin filling hole 18 is circular.

A space surrounded by the substrate 11, the optical element 13, the ferrule 15, the distal end of the optical fiber 50, and the like is filled with the resin 19. It is preferable that the resin 19 be set to have substantially the same the refractive index as the core of the optical fiber 50. Normally, since the refractive index of the core of the optical fiber 50 is about 1.4 to 1.6, it is preferable to use a resin having a refractive index of about 1.4 to 1.6 as the resin 19. Specifically, a resin having a refractive index of about 1.4 to 1.6 is used among epoxy resins and acrylic resins. This is to suppress the loss of the optical signal that is output from the optical element 13.

Next, a method for manufacturing the optical transmission module according to the first embodiment will be described with reference to FIGS. 5A to 5C.

Figure 5A:
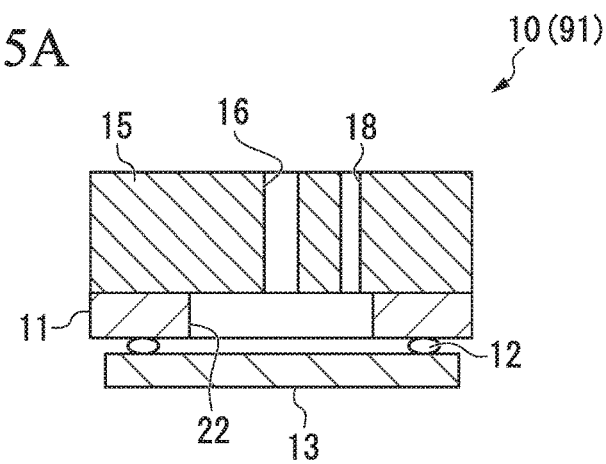
FIG. 5A is a view showing a method for manufacturing an optical transmission module according to the first embodiment.

FIG. 5A is a diagram showing the E/O converter 10 before the optical fiber 50 is inserted into the optical fiber insertion hole 16. The optical element 13 is mounted on the substrate 11 to close the lower surface side opening of the substrate 11 by a method such as flip chip mounting or the like. The ferrule 15 is fixed to the substrate 11 to close the upper surface side opening of the substrate 11.

Figure 5B:
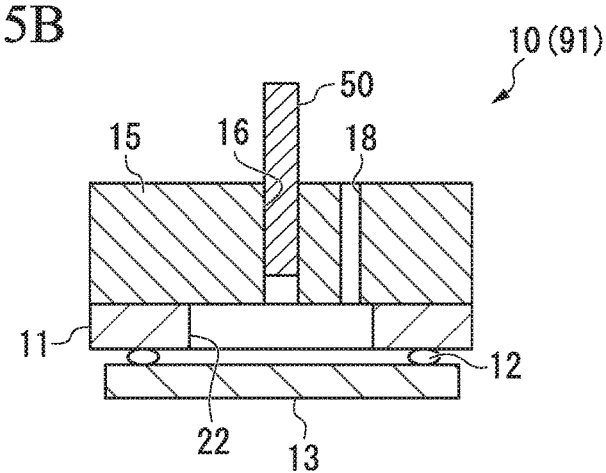
FIG. 5B is a view showing the method for manufacturing the optical transmission module according to the first embodiment.

FIG. 5B is a diagram showing the E/O converter 10 (optical transmission module structure) after the optical fiber 50 is inserted into the optical fiber insertion hole 16. The optical fiber 50 is inserted into the optical fiber insertion hole 16 in the E/O converter 10 in the state of FIG. 5A.

Figure 5C:
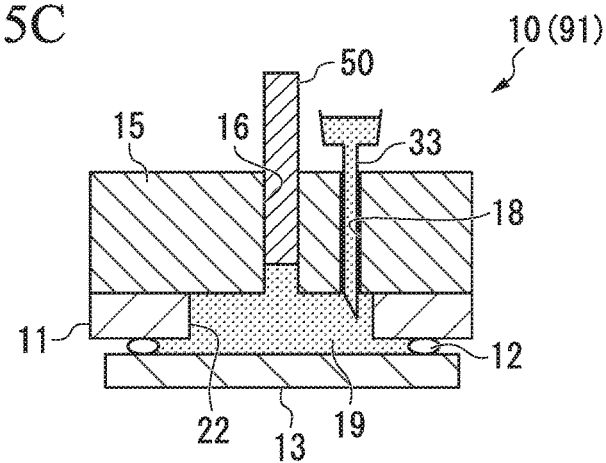
FIG. 5C is a view showing the method for manufacturing the optical transmission module according to the first embodiment.

FIG. 5C is a diagram showing the filling of the resin 19. The filling needle 33 is inserted into the resin filling hole 18 and filled with the resin 19. As a result, the space surrounded by the substrate 11, the optical element 13, the ferrule 15, the distal end of the optical fiber 50, and the like is filled with the resin 19. Thereafter, the filling needle 33 is extracted and the E/O converter 10 is completed.

In the E/O converter 10 according to the first embodiment, the optical fiber insertion hole 16 and the resin filling hole 18 are disposed to be spaced apart from each other. Therefore, after inserting the optical fiber 50 into the optical fiber insertion hole 16, even if the resin 19 is filled using the filling needle 33, the work efficiency does not degrade, and the distal end of the filling needle 33 does not damage the optical fiber 50.

In the first embodiment, the shape of the I-I cross section of the optical fiber insertion hole 16 in FIG. 3 has been described as a circle, but the shape may be a polygon such as a triangle or a quadrangle, the shape may be an ellipse, and any shape may be provided as long as the optical fiber 50 can be inserted.

In the first embodiment, the E/O converter 10 has been described as an example of the optical transmission module. However, if the optical element 13 is a photoelectric conversion element such as a photodiode (PD), the optical transmission module is an O/E converter 91.

In this case, the O/E converter 91 converts the optical signal transmitted by the optical fiber 50 into an electric signal by the PD which is the optical element 13. Thereafter, an electric signal is transmitted to the substrate 11 via the bump 12. The electric signal transmitted to the substrate 11 is transmitted to the connector 93 via the metal wiring 50M.

In the following embodiments, the E/O converters 10A to 10J will be described as an example of the optical transmission module. If the optical element 13 is replaced with the PD from the VCSEL as described above, the optical transmission modules are the O/E converters 91A to 91J, respectively.

Second Embodiment

Next, a second embodiment will be described with reference to FIGS. 6 and 7. A drawing showing the endoscope and a drawing showing the outline of the insertion unit would be the same as those of FIGS. 1 and 2, and therefore will not be provided. Repeated explanation of content of the first embodiment will not be provided.

Figure 6:
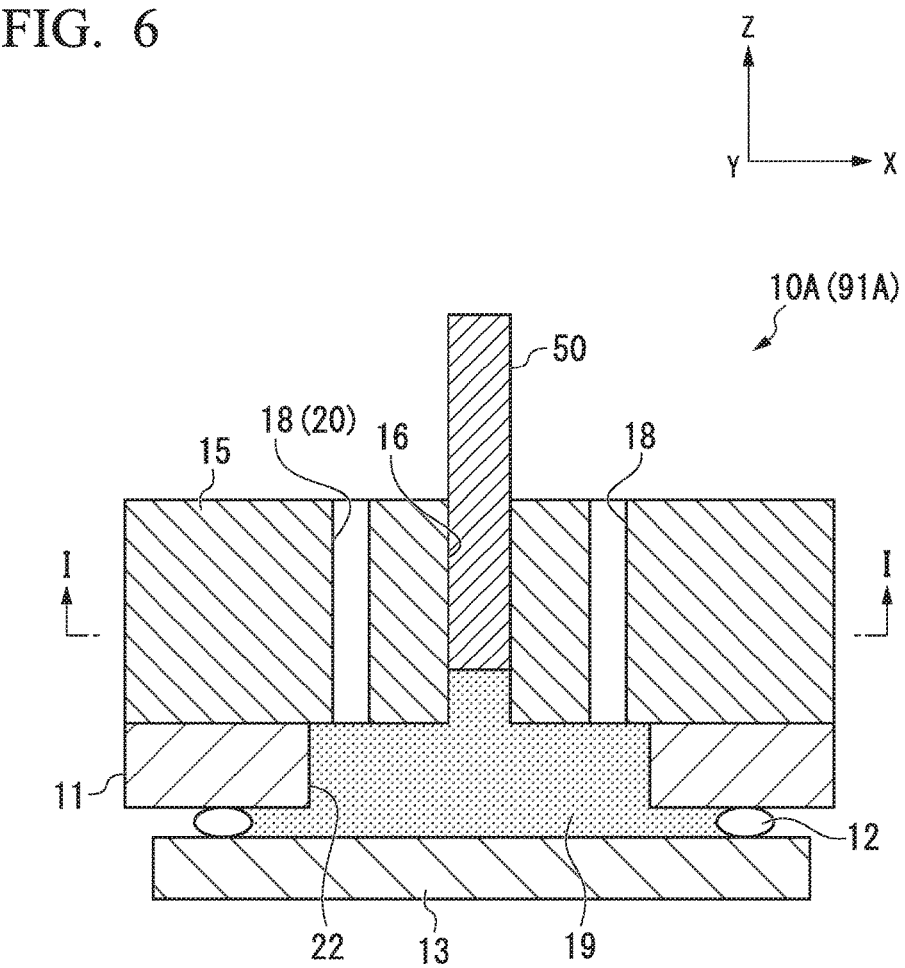
FIG. 6 is a cross-sectional view of an optical transmission module according to a second embodiment.
Figure 7:
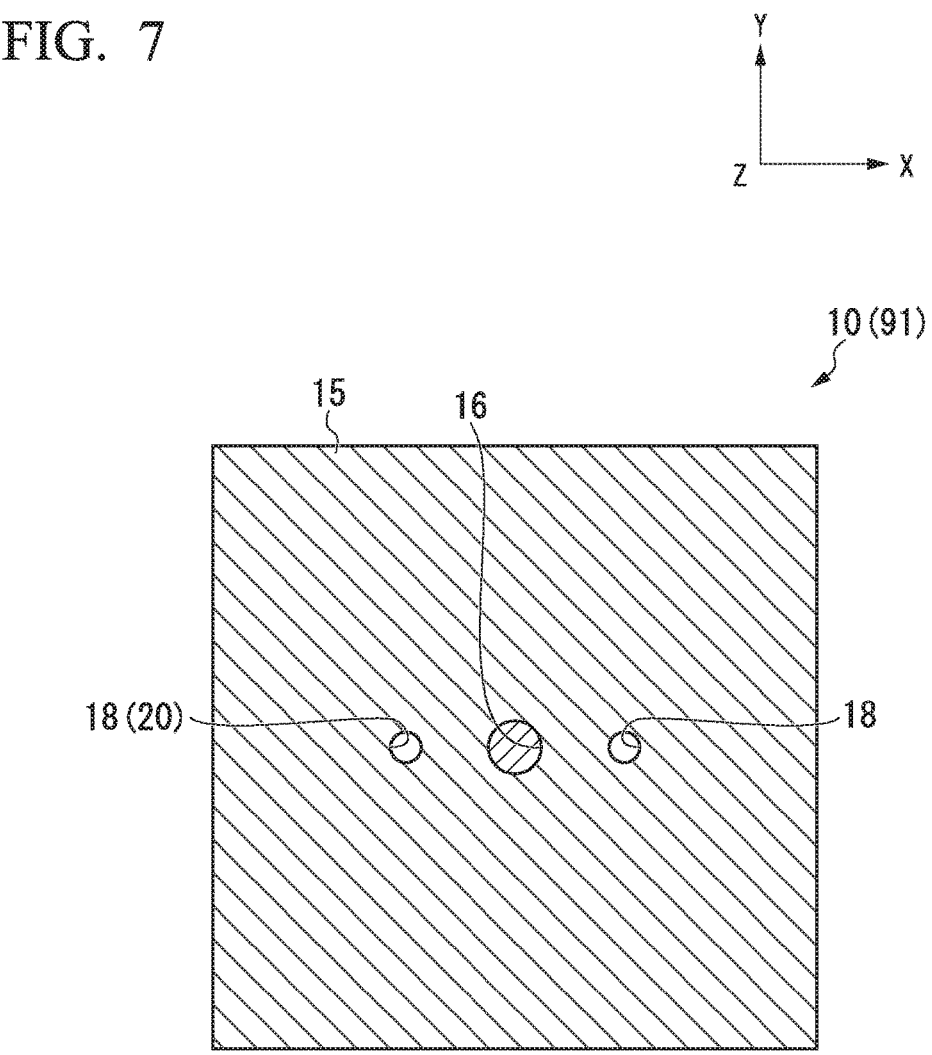
FIG. 7 is a cross-sectional view taken along a line I-I of FIG. 6.

FIG. 6 is a cross-sectional view of the optical transmission module according to the second embodiment. FIG. 7 is a cross-sectional view taken along a line I-I of FIG. 6.

The E/O converter 10A is different from the E/O converter 10 according to the first embodiment in that two resin filling holes 18 are provided. When the E/O converter 10A is viewed from the Z-axis direction, the two resin filling holes 18 are disposed at the point-symmetrical positions with respect to the center of the optical fiber insertion hole 16. The two resin filling holes 18 may not be disposed at the point-symmetrical positions with respect to the center of the optical fiber insertion hole 16. Although the case of the two resin filling holes 18 is described, it is needless to say that three or more resin filling holes 18 may be formed.

By providing the two resin filling holes 18 in this manner, it is possible to make the resin 19 being filled from the two resin filling holes 18 such that the work efficiency is improved.

One of the two resin filling holes 18 may be used as an air discharge hole 20. In this case, the resin 19 is filled from one resin filling hole 18. When the resin 19 is filled, the air in the space surrounded by the substrate 11, the optical element 13, the ferrule 15, the distal end of the optical fiber 50 and the like is discharged from the air discharge hole 20. It is possible to more reliably discharge the air in the space surrounded by the substrate 11, the optical element 13, the ferrule 15, the distal end of the optical fiber 50 and the like. That is, it is possible to improve the work efficiency when the resin 19 is filled.

Third Embodiment

Next, a third embodiment will be described based on FIG. 8. A drawing showing the endoscope and a drawing showing the outline of the insertion unit would be the same as those of FIGS. 1 and 2, and therefore will not be provided. Repeated explanation of content of the first embodiment will not be provided.

Figure 8:
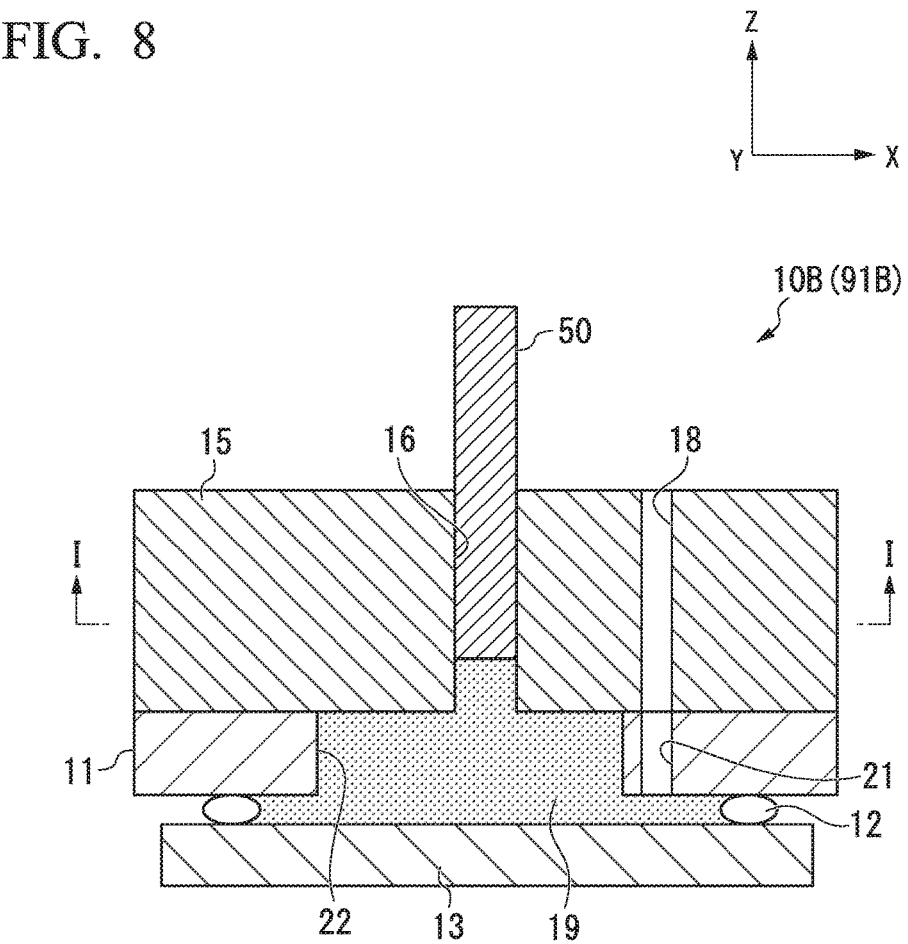
FIG. 8 is a cross-sectional view of an optical transmission module according to a third embodiment.

FIG. 8 is a cross-sectional view of the optical transmission module according to the third embodiment. Further, a cross-sectional view taken along a line I-I of FIG. 8 is substantially the same as that of FIG. 4 and will not be described. The E/O converter 10B is different from the E/O converter 10 according to the first embodiment in that a through-hole 21 is provided in the substrate 11.

The through-hole 21 penetrates from the first surface (the surface on which the optical element 13 is disposed) of the substrate 11 to a second surface (the surface on which the ferrule 15 is disposed) opposite to the first surface, and is communicated with the resin filling hole 18. Since the through-hole 21 is formed in a direction orthogonal to the plane direction of the substrate 11, the through-hole 21 and the resin filling hole 18 communicate with each other. When the resin 19 is filled from the resin filling hole 18, the resin 19 is filled from the first surface of the substrate 11 through the through-hole 21.

In the E/O converter 10 B, the resin 19 is filled from the first surface of the substrate 11. The first surface of the substrate 11 is the lower part of the space surrounded by the substrate 11, the optical element 13, the ferrule 15, the distal end of the optical fiber 50, and the like, and since the resin 19 is filled from the lower part, it is possible to more reliably fill the resin 19 in the space surrounded by the substrate 11, the optical element 13, the ferrule 15, the distal end of the optical fiber 50, and the like.

Fourth Embodiment

Next, a fourth embodiment will be described with reference to FIGS. 9 and 10. Further, a drawing showing the endoscope and a drawing showing the outline of the insertion unit would be the same as those of FIGS. 1 and 2, and therefore will not be provided. Further, repeated explanation of content of the first embodiment will not be provided.

Figure 9:
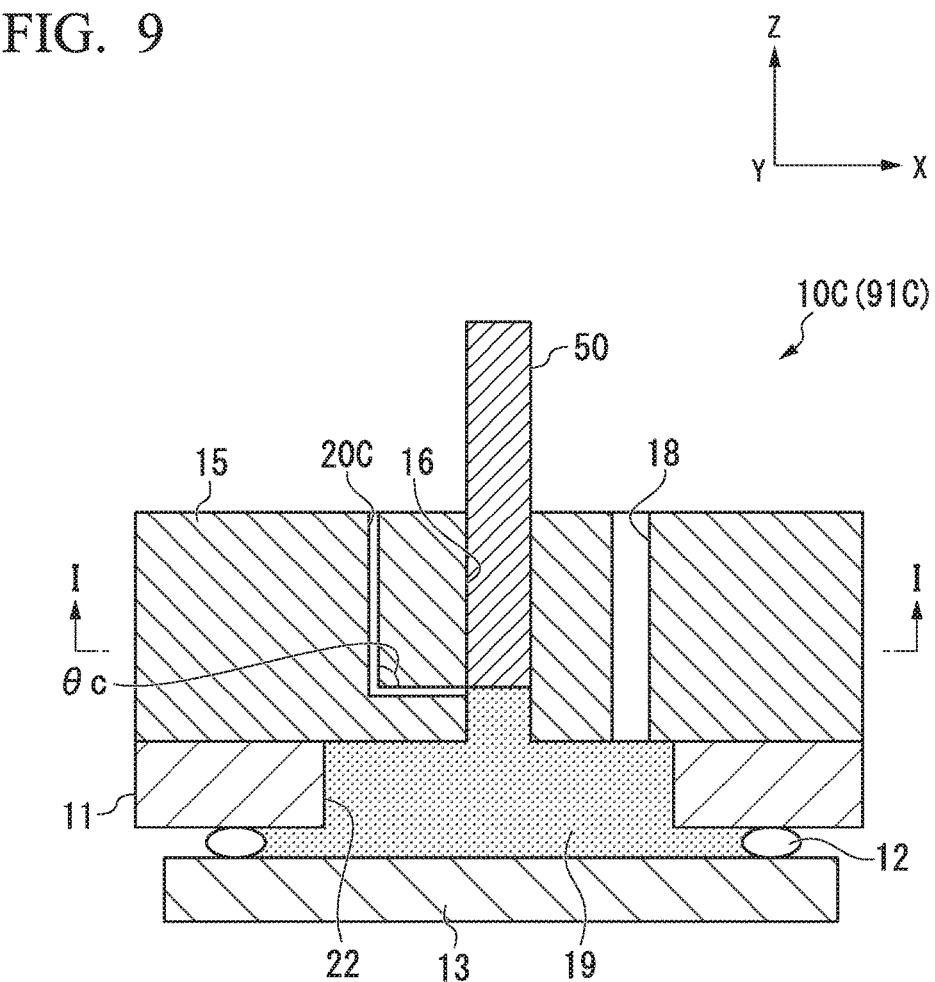
FIG. 9 is a cross-sectional view of an optical transmission module according to a fourth embodiment.
Figure 10:
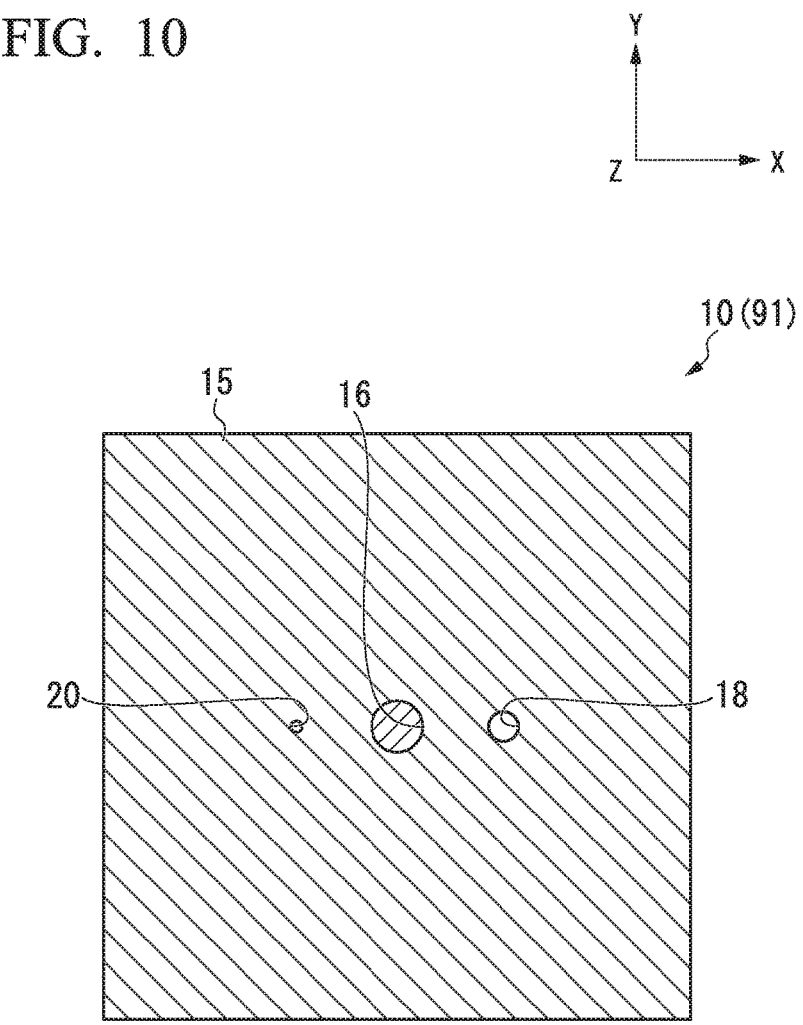
FIG. 10 is a cross-sectional view taken along a line I-I of FIG. 9.

FIG. 9 is a cross-sectional view of the optical transmission module according to the fourth embodiment. FIG. 10 is a cross-sectional view taken along a line I-I of FIG. 9. The E/O converter 10C is different from the first E/O converter 10 in that an air discharge hole 20C is included.

In the air discharge hole 20C, the cross-sectional shape of the Z-X plane is an L-shape. The air discharge hole 20C penetrates from the front end side (the side on which the optical element 13 is not disposed) of the ferrule 15 to a position at which the distal end of the optical fiber 50 is disposed. One end of the air discharge hole 20C is disposed in communication with the optical fiber insertion hole 16 and close to the distal end of the optical fiber 50. In the air discharge hole 20C, the cross-sectional shape of the Z-X plane is not necessarily an L-shape. In other words, an air discharge hole angle $\theta_C$ is not necessarily 90°, and may be, for example, $90°<\theta_C<150°$.

In the E/O converter 10C, when the resin 19 is filled from the resin filling hole 18, the space surrounded by the substrate 11, the optical element 13, the ferrule 15, the distal end of the optical fiber 50, and the like is filled with the resin 19. At that time, the air in the space surrounded by the substrate 11, the optical element 13, the ferrule 15, the distal end of the optical fiber 50, and the like is released from the air discharge hole 20C.

One end of the air discharge hole 20C is disposed in communication with the optical fiber insertion hole 16 and close to the distal end of the optical fiber 50. Until the resin 19 is filled up to the vicinity of the distal end of the optical fiber 50, the air discharge hole 20C is not blocked by the resin 19. That is, until just before the filling of the resin 19 is completed, the air discharge hole 20C can discharge the air, and can more reliably discharge the air that was in the space surrounded by the substrate 11, the optical element 13, the ferrule 15, the distal end of the optical fiber 50, and the like.

Fifth Embodiment

Next, a fifth embodiment will be described with reference to FIG. 11. A drawing showing the endoscope and a drawing showing the outline of the insertion unit would be the same as those of FIGS. 1 and 2, and therefore will not be provided. Repeated explanation of content of the first embodiment will not be provided.

Figure 11:
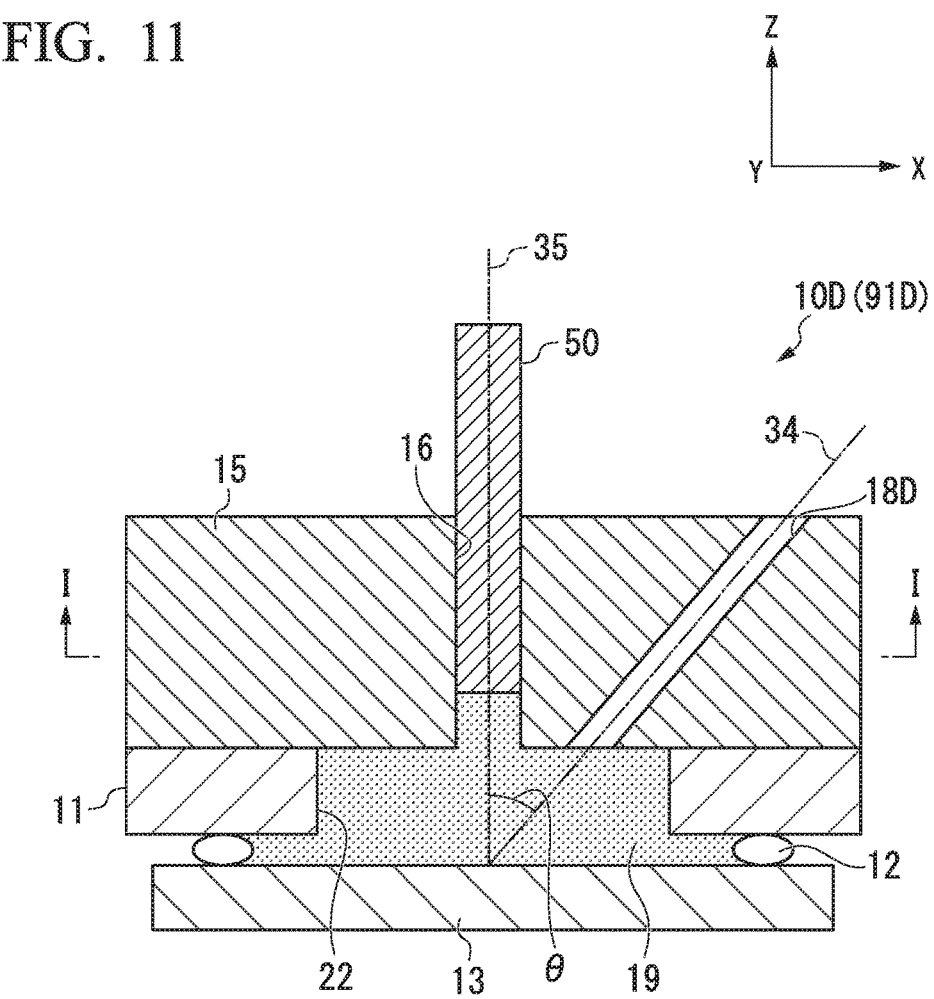
FIG. 11 is a cross-sectional view of an optical transmission module according to a fifth embodiment.

FIG. 11 is a cross-sectional view of the optical transmission module according to the fifth embodiment. Since the cross-sectional view taken from the line I-I of FIG. 11 is substantially the same as that of FIG. 4, it will not be described. The E/O converter 10D is different from the first E/O converter 10 in that the resin filling hole 18D is not a hole parallel to the Z-axis direction (a direction perpendicular to the plane direction of the substrate 11).

The axis 34 of the resin filling hole 18D forms a predetermined angle $\theta$ ($0°<\theta<90°$) with the optical fiber insertion hole 16 or the axis 35 of the optical fiber 50. In this way, since the distance between the resin filling hole 18D and the optical fiber insertion hole 16 increases, it is possible to further enhance the work efficiency when the resin 19 is filled.

As the predetermined angle $\theta$ increases, since the distance between the optical fiber insertion hole 16 and the resin filling hole 18D increases, the work efficiency when the resin 19 is filled can be improved. However, if the predetermined angle $\theta$ is too large, it takes time to make the resin 19 being filled. The predetermined angle $\theta$ is preferably in the range of $22.5°\leq\theta\leq67.5°$. More preferably, the predetermined angle $\theta$ is in the range of $45°\leq\theta\leq60°$.

Next, a modified example of the fifth embodiment will be described with reference to FIG. 12. Further, a drawing showing the endoscope and a drawing showing the outline of the insertion unit would be the same as those of FIGS. 1 and 2, and therefore will not be provided.

Figure 12:
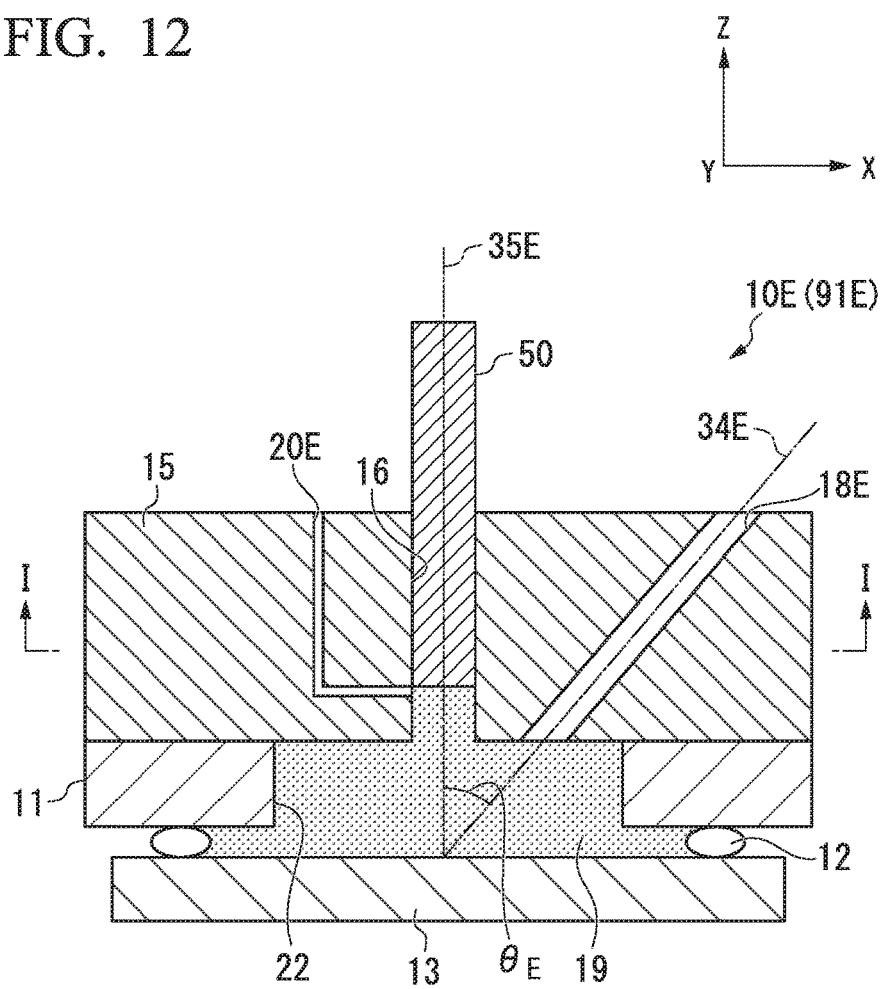
FIG. 12 is a cross-sectional view of an optical transmission module according to a modified example of the fifth embodiment.

FIG. 12 is a cross-sectional view of an optical transmission module according to a modified example of the fifth embodiment. Since the cross-sectional view taken from the line I-I of FIG. 12 is substantially the same as that of FIG. 10, it will be omitted. The E/O converter 10E includes a resin filling hole 18E and an air discharge hole 20E.

Since the resin filling hole 18E is almost the same as the resin filling hole 18D shown in FIG. 11, a detailed description thereof will be omitted. Since the air discharge hole 20E is almost the same as the air discharge hole 20C shown in FIG. 9, a detailed description thereof will be omitted.

The axis 34 E of the resin filling hole 18E forms a predetermined angle $\theta_E$ ($0°<\theta<90°$) with the axis 35E of the optical fiber insertion hole 16. Therefore, the distance between the resin filling hole 18E and the optical fiber insertion hole 16 increases, and the work efficiency can be improved when the resin 19 is filled.

One end of the air discharge hole 20E is disposed in communication with the optical fiber insertion hole 16 and close to the distal end of the optical fiber 50. Therefore, until the resin 19 is filled up to the vicinity of the distal end of the optical fiber 50, the air discharge hole 20E is not blocked by the resin 19. That is, until just before the filling of the resin 19 is completed, the air discharge hole 20E can discharge the air, and can more reliably discharge the air that was in a space surrounded by the substrate 11, the optical element 13, the ferrule 15, the distal end of the optical fiber 50, and the like.

As described above, the E/O converter 10E can further enhance the work efficiency when the resin is filled, and it is possible to more reliably discharge the air that was in the space surrounded by the substrate 11, the optical element 13, the ferrule 15, the distal end of the optical fiber 50 and the like.

Sixth Embodiment

Next, a sixth embodiment will be described with reference to FIG. 13. A drawing showing the endoscope and a drawing showing the outline of the insertion unit would be the same as those of FIGS. 1 and 2, and therefore will be omitted.

Figure 13:
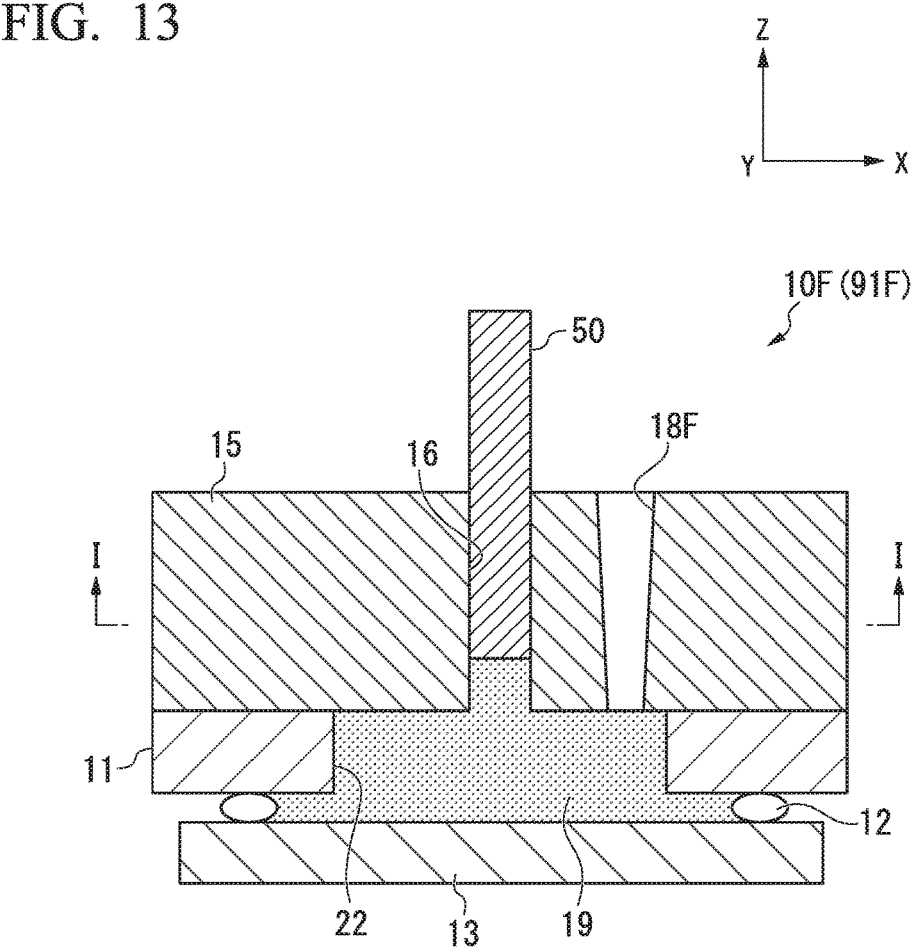
FIG. 13 is a cross-sectional view of an optical transmission module according to a sixth embodiment.

FIG. 13 is a cross-sectional view of the optical transmission module in the sixth embodiment. Since the cross-sectional view taken from the line I-I of FIG. 13 is substantially the same as that of FIG. 4, it will be omitted. The E/O converter 10F is different from the first E/O converter 10 in that the resin filling hole 18F has a tapered shape.

The resin filling hole 18F has a tapered shape so that the diameter of the hole decreases from the front end side (the side on which the optical element 13 is not disposed) to the rear end side (the side on which the optical element 13 is disposed) of the ferrule 15. In this way, it is easier to insert the filling needle 33 into the resin filling hole 18F when the resin 19 is filled via the filling needle 33, and it is possible to further improve the work efficiency when the resin 19 is filled.

Seventh Embodiment

Next, a seventh embodiment will be described with reference to FIGS. 14 and 15. A drawing showing the endoscope and a drawing showing the outline of the insertion unit would be the same as those of FIGS. 1 and 2, and therefore will be omitted.

Figure 14:
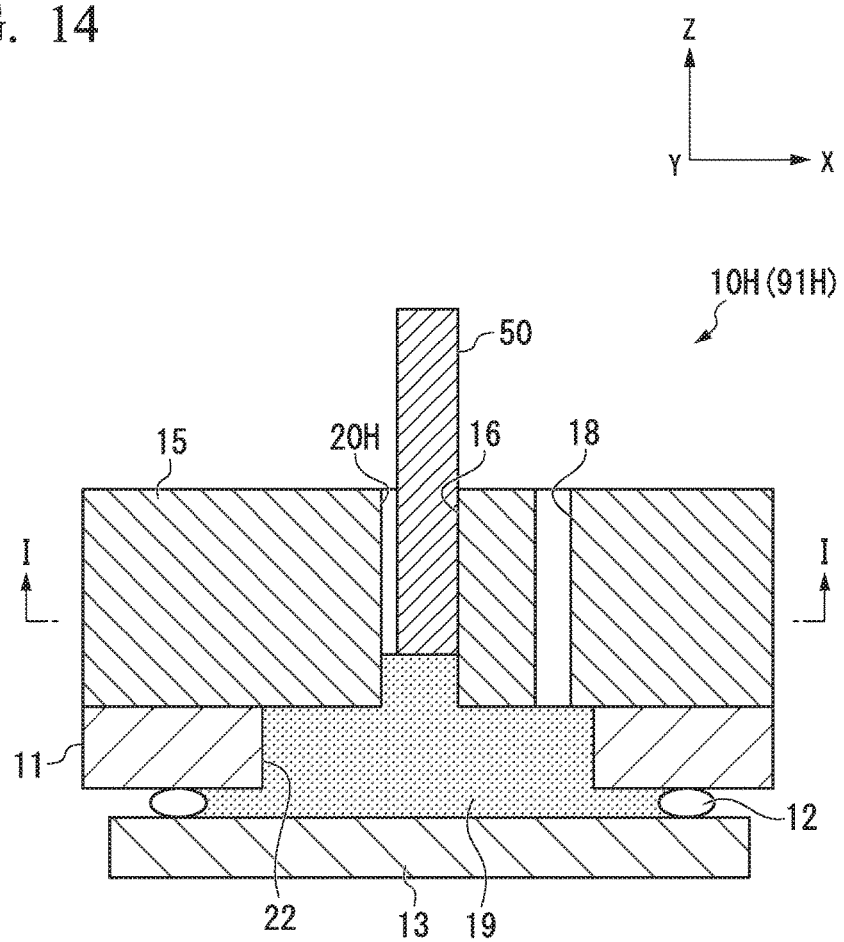
FIG. 14 is a cross-sectional view of an optical transmission module according to a modified example of the seventh embodiment.
Figure 15:
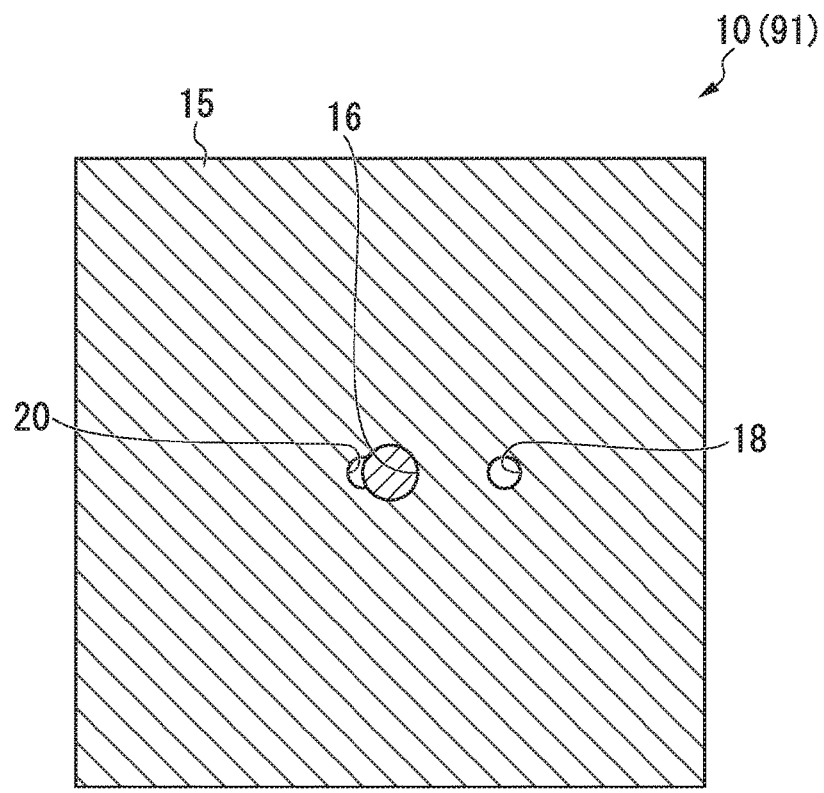
FIG. 15 is a sectional view taken along a line I-I in FIG. 14.

FIG. 14 is a cross-sectional view of the optical transmission module according to the seventh embodiment. Further, FIG. 15 is a cross-sectional view taken along a line I-I of FIG. 14.

The E/O converter 10H includes an air discharge hole 20H. The air discharge hole 20H communicates with the optical fiber insertion hole 16 and is formed along the optical fiber insertion hole. Accordingly, when the resin 19 is filled from the resin filling hole 18, it is possible to more reliably discharge the air that was in the space surrounded by the substrate 11, the optical element 13, the ferrule 15, and the distal end of the optical fiber 50.

Eighth Embodiment

Next, an eighth embodiment will be described with reference to FIG. 16. Further, since a drawing showing the endoscope and a drawing showing the outline of the insertion unit would be the same as those of FIGS. 1 and 2, they will be omitted.

Figure 16:
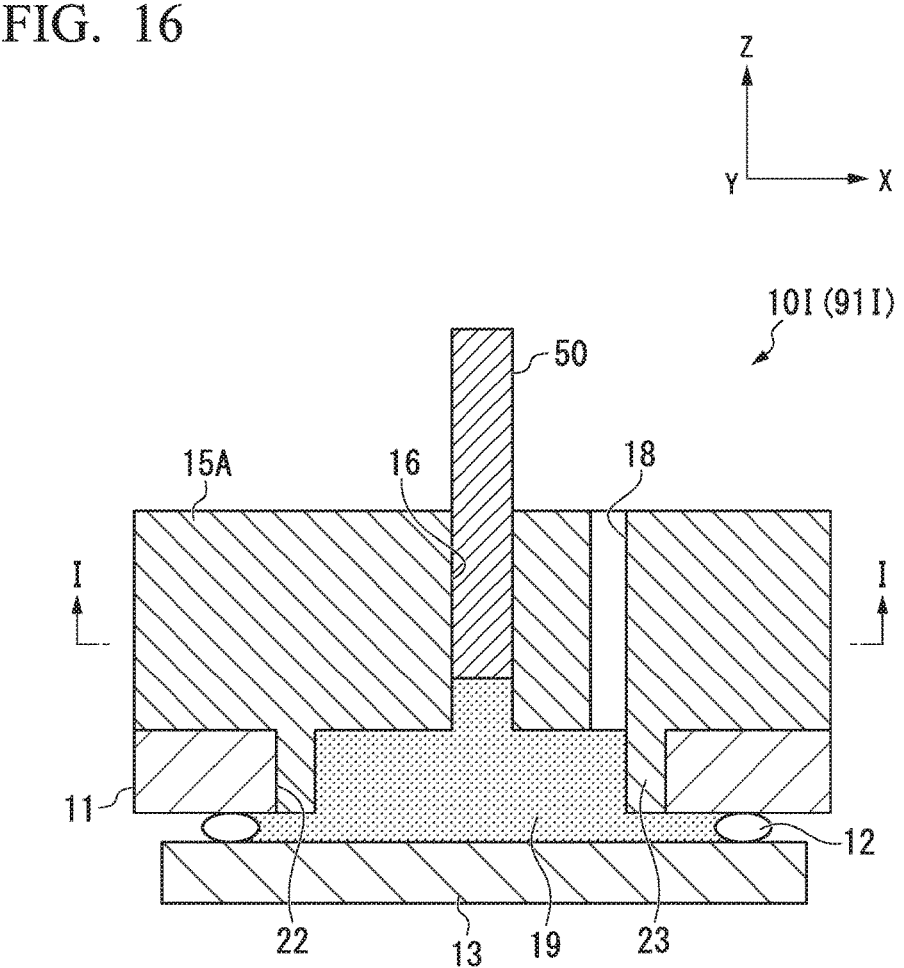
FIG. 16 is a cross-sectional view of an optical transmission module according to an eighth embodiment.

FIG. 16 is a cross-sectional view of the optical transmission module according to the eighth embodiment.

The E/O converter 10I differs from that of FIG. 3 in the shape of the ferrule. The ferrule 15A has a shape having an annular protrusion 23 fitted to the opening portion of the substrate 11.

The resin 19 is filled into a space surrounded by the substrate 11, the optical element 13 and the distal end of the optical fiber 50 via the ferrule 15A.

According to the eighth embodiment, since the ferrule 15A and the substrate 11 can be easily positioned and fixed before the resin 19 is filled, manufacturing of the optical transmission module can be further simplified. Even in an optical transmission module structure not including the optical fiber 50 and the resin 19, the distribution transaction thereof is suitable.

Ninth Embodiment

Next, a ninth embodiment will be described with reference to FIG. 17. Since a drawing showing the endoscope and a drawing showing the outline of the insertion unit would be the same as those of FIGS. 1 and 2, they will be omitted.

Figure 17:
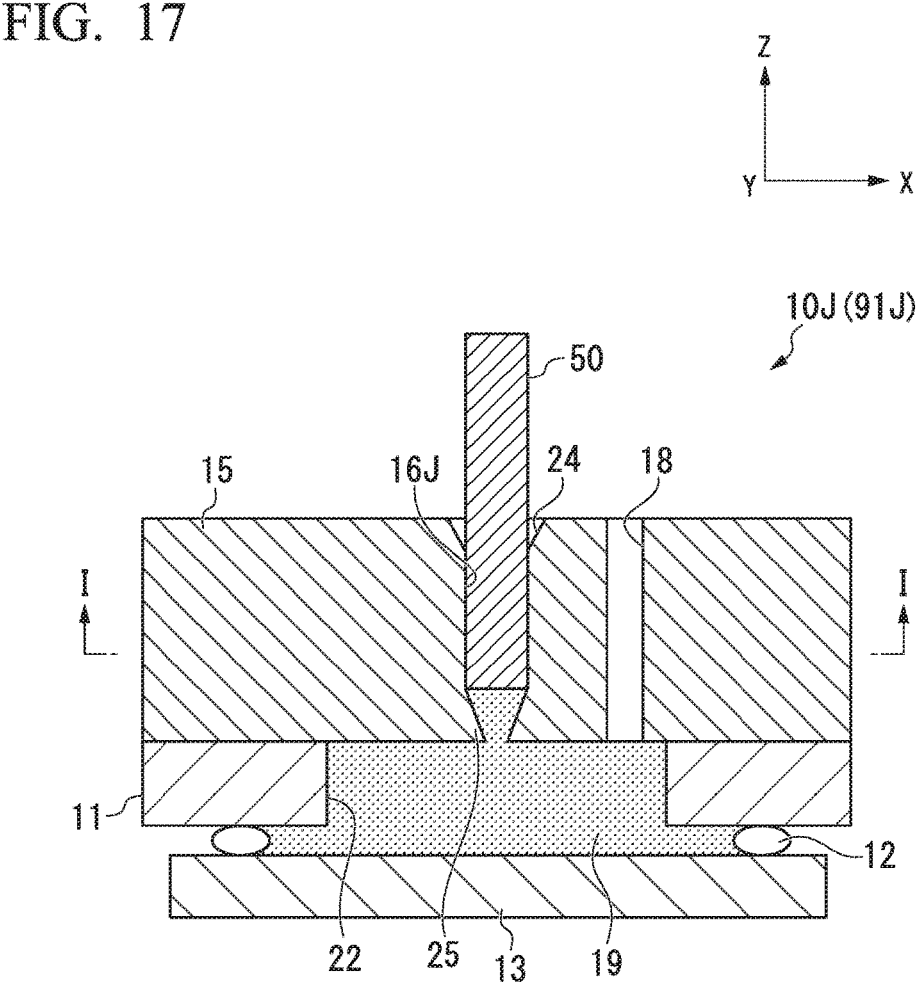
FIG. 17 is a cross-sectional view of an optical transmission module according to a ninth embodiment.

FIG. 17 is a cross-sectional view of the optical transmission module according to the ninth embodiment.

An E/O converter 10J is different from that shown in FIG. 3 in the shape of the optical fiber insertion hole. An optical fiber insertion hole 16J has an outward tapered portion 24 on the rear end side (the side on which the optical element 13 is not disposed) and an inward tapered portion 25 on the front end side (the side on which the optical element 13 is disposed).

According to the ninth embodiment, by providing the outward tapered portion 24, the optical fiber 50 can be easily inserted into the optical fiber insertion hole 16J. Further, by providing the inward tapered portion 25, it is possible to easily position the optical fiber 50 in the optical fiber insertion hole 16J.

The inward tapered portion 25 may be formed integrally with the ferrule 15 or may be formed separately from the ferrule 15.

Although embodiments and modified examples of the present invention have been described above in detail with reference to the drawings, the specific configuration is not limited to the above-described embodiments and the like, and design changes within the scope that does not depart from the gist of the present invention are also included.

In the above-described embodiments and the like, the optical transmission module is applied to a medical endoscope, but the present invention can also be applied to an industrial endoscope.

The embodiments of the invention have been described above with reference to the drawings, but specific structures of the invention are not limited to the embodiments and may include various modifications without departing from the scope of the invention. The invention is not limited to the above-mentioned embodiments and is limited only by the accompanying claims.

What is claimed is:

1. An optical transmission module comprising:
   a substrate having an opening penetrating in a vertical direction orthogonal to a plane direction;
   an optical element which is disposed to close the opening on a lower surface side of the substrate and the optical element converts an electric signal into an optical signal or converts the optical signal into the electric signal;

an optical fiber which transmits the optical signal;

a ferrule which is disposed to close the opening on an upper surface side of the substrate, the ferrule having an optical fiber insertion hole through which the optical fiber is inserted and held; and a resin filled into a space surrounded at least by the substrate, the optical element, the ferrule, and a distal end of the optical fiber, wherein the ferrule has a resin filling hole formed to be spaced apart from the optical fiber insertion hole to fill the space with the resin, and an angle formed by an axis of the optical fiber insertion hole and an axis of the resin filling hole is greater than 0° and less than 90°.

2. The optical transmission module according to claim 1, wherein the ferrule has a plurality of resin filling holes.

3. The optical transmission module according to claim 1, wherein the ferrule further includes an air discharge hole which discharges air in the space to outside.

4. The optical transmission module according to claim 2, wherein the ferrule further includes an air discharge hole which discharges air in the space to outside.

5. The optical transmission module according to claim 3, wherein an end of the air discharge hole is disposed in communication with the optical fiber insertion hole and close to the distal end of the optical fiber.

6. The optical transmission module according to claim 1, wherein the angle formed by the axis of the optical fiber insertion hole and the axis of the resin filling hole is equal to or more than 22.5° and equal to or less than 67.5°.

7. The optical transmission module according to claim 6, wherein the angle formed by the axis of the optical fiber insertion hole and the axis of the resin filling hole is equal to or more than 45° and equal to or less than 60°.

8. The optical transmission module according to claim 3, wherein the air discharge hole communicates with the optical fiber insertion hole and is formed along the optical fiber insertion hole.

9. An imaging apparatus comprising: an imaging element which picks up an image of a subject; and the optical transmission module according to claim 1 which converts an imaging signal from the imaging element into an optical signal or converts the optical signal into an electric signal.

10. An optical transmission module comprising:

a substrate having an opening penetrating in a vertical direction orthogonal to a plane direction;

an optical element which is disposed to close the opening on a lower surface side of the substrate and the optical element converts an electric signal into an optical signal or converts the optical signal into the electric signal;

an optical fiber which transmits the optical signal;

a ferrule which is disposed to close the opening on an upper surface side of the substrate, the ferrule having an optical fiber insertion hole through which the optical fiber is inserted and held; and a resin filled into a space surrounded at least by the substrate, the optical element, the ferrule, and a distal end of the optical fiber, wherein the ferrule has a resin filling hole formed to be spaced apart from the optical fiber insertion hole to fill the space with the resin, and wherein an axis of the optical fiber insertion hole and an axis of the resin filling hole are parallel to each other.

11. The optical transmission module according to claim 10, wherein the ferrule has a plurality of resin filling holes.

12. The optical transmission module according to claim 10, wherein the ferrule further includes an air discharge hole which discharges air in the space to outside.

13. The optical transmission module according to claim 12, wherein an end of the air discharge hole is disposed in communication with the optical fiber insertion hole and close to the distal end of the optical fiber.

14. The optical transmission module according to claim 10, wherein the substrate has a through-hole extending in a direction orthogonal to the plane direction, and the through-hole and the resin filling hole communicate with each other.

15. The optical transmission module according to claim 12, wherein the air discharge hole communicates with the optical fiber insertion hole and is formed along the optical fiber insertion hole.

16. An imaging apparatus comprising:

an imaging element which picks up an image of a subject; and the optical transmission module according to claim 10, which converts an imaging signal from the imaging element into an optical signal or converts the optical signal into an electric signal.

* * * * *